(12) United States Patent
Macknik et al.

(10) Patent No.: US 11,903,720 B2
(45) Date of Patent: Feb. 20, 2024

(54) SYSTEM AND METHOD FOR DETECTING NEUROLOGICAL DISEASE

(71) Applicants: DIGNITY HEALTH, San Francisco, CA (US); LE CENTRE NATIONAL DE LA RECHERCHE SCIENTIFIQUE, Paris (FR)

(72) Inventors: Stephen L. Macknik, Anthem, AZ (US); Susana Martinez-Conde, Anthem, AZ (US); Zoi Kapoula, Paris (FR); Jorge Otero-Millan, Baltimore, MD (US)

(73) Assignees: DIGNITY HEALTH, San Francisco, CA (US); LE CENTRE NATIONAL DE LA RECHERCHE SCIENTIFIQUE (FR)

( * ) Notice: Subject to any disclaimer, the term of this patent is extended or adjusted under 35 U.S.C. 154(b) by 476 days.

(21) Appl. No.: 16/741,549

(22) Filed: Jan. 13, 2020

(65) Prior Publication Data
US 2020/0146611 A1 May 14, 2020

Related U.S. Application Data

(63) Continuation of application No. 15/958,403, filed on Apr. 20, 2018, now Pat. No. 10,537,276, which is a (Continued)

(51) Int. Cl.
*A61B 5/00* (2006.01)
*A61B 3/00* (2006.01)
*A61B 3/113* (2006.01)

(52) U.S. Cl.
CPC .......... *A61B 5/4088* (2013.01); *A61B 3/0025* (2013.01); *A61B 3/0091* (2013.01); (Continued)

(58) Field of Classification Search
CPC ..... A61B 3/0025; A61B 3/0091; A61B 3/113; A61B 5/163; A61B 5/4088; A61B 5/4842; A61B 5/4848
See application file for complete search history.

(56) References Cited

U.S. PATENT DOCUMENTS

| | | |
|---|---|---|
| 4,815,839 A | 3/1989 | Waldorf |
| 5,137,345 A | 8/1992 | Waldorf |

(Continued)

FOREIGN PATENT DOCUMENTS

| | | |
|---|---|---|
| JP | H06154167 A | 6/1994 |
| JP | 2001-309890 A | 11/2001 |

(Continued)

OTHER PUBLICATIONS

Japan Patent Office, Notification for Reason of Refusal for application 2019-065170, dated Apr. 21, 2020. With translation.
(Continued)

*Primary Examiner* — Jack Dinh
(74) *Attorney, Agent, or Firm* — QUARLES & BRADY LLP

(57) ABSTRACT

A system and method of detecting eye movements of a subject for the diagnosis of neurological disorders. The method includes tracking eye movements of the subject, identifying microsaccades from the tracked eye movements, and characterizing microsaccade dynamics of the identified microsaccades to determine one or more parameters, such as microsaccade direction, microsaccade velocity, microsaccade magnitude, microsaccadic peak velocity-magnitude relationship, microsaccade duration, and intersaccadic intervals. The method also includes comparing the one or more determined parameters with a corresponding control parameter, assessing the comparison to determine differences between the one or more determined parameters and the corresponding control parameters, and generating a report
(Continued)

including the diagnosis of neurological disorder based on the assessment.

15 Claims, 4 Drawing Sheets

Related U.S. Application Data continuation of application No. 14/893,552, filed as application No. PCT/US2014/035082 on Apr. 23, 2014, now Pat. No. 9,962,119.

(60) Provisional application No. 61/829,898, filed on May 31, 2013.

(52) U.S. Cl.
CPC ............ *A61B 3/113* (2013.01); *A61B 5/4842* (2013.01); *A61B 5/4848* (2013.01)

(56) References Cited

U.S. PATENT DOCUMENTS

| | | |
|---|---|---|
| 5,382,989 A | 1/1995 | Uomori |
| 7,309,125 B2 | 12/2007 | Pugach |
| 8,348,428 B2 | 1/2013 | Martinez-Conde |
| 8,668,337 B2 | 3/2014 | Waldorf |
| 8,721,081 B2 | 5/2014 | Martinez-Conde |
| 9,101,312 B2 | 8/2015 | Waldorf |
| 9,301,679 B2 | 4/2016 | Martinez-Conde |
| 11,013,441 B2 | 5/2021 | Samadani |
| 2003/0028081 A1 | 2/2003 | Blazey |
| 2007/0013868 A1 | 1/2007 | Pugach |
| 2009/0198148 A1 | 8/2009 | Lonky |
| 2010/0191156 A1 | 7/2010 | Sakamoto |
| 2010/0208205 A1 | 8/2010 | Tseng |
| 2010/0277693 A1 | 11/2010 | Martinez-Conde |
| 2012/0059282 A1 | 3/2012 | Agichtein |
| 2012/0081666 A1 | 4/2012 | Kiderman |
| 2016/0022137 A1 | 1/2016 | Wetzel |

FOREIGN PATENT DOCUMENTS

| | | |
|---|---|---|
| WO | 2010107568 A1 | 9/2010 |
| WO | 2012103470 A2 | 8/2012 |

OTHER PUBLICATIONS

Canadian Intellectual Property Office. Office Action for application 2,912,426, dated Dec. 10, 2020. 6 pages.
Zola, S. M., et al. "A behavioral task predicts conversion to mild cognitive impairment and Alzheimer's disease." American Journal of Alzheimer's Disease & Other Dementias® 28.2 (2013): 179-184.
International Search Report and Written Opinion dated Sep. 29, 2014 in connection with PCT/US2014/35082.
Ziad M. Hafed et al., Microsaccades as an Overt Measure of Covert Attention Shifts, Vision Research 42 (2002) 2533-2545.
European Patent Office. Extended European Search Report for application 21190322.4, dated Nov. 15, 2021. 8 pages.

SYSTEM AND METHOD FOR DETECTING NEUROLOGICAL DISEASE

CROSS-REFERENCE TO RELATED APPLICATION

This application is a continuation of U.S. patent application Ser. No. 15/958,403, filed Apr. 20, 2018, which is a continuation of U.S. patent application Ser. No. 14/893,552 filed Nov. 24, 2015, which represents the national stage entry of PCT International Application No. PCT/US2014/035082 filed Apr. 23, 2014, which claims the benefit of U.S. Provisional Patent Application Ser. No. 61/829,898, filed May 31, 2013, in which the contents of all of the applications are incorporated herein by reference in their entirety for all purposes.

BACKGROUND OF THE INVENTION

The present application is directed to monitoring eye movements to detect neurological disease. In particular, the present application is directed to analyzing microsaccades for detecting neurological disorder or neurodegenerative diseases, such as Alzheimer's Disease and mild cognitive impairment.

Alzheimer's Disease (AD) is the most common form of dementia, accounting for 50 to 70 percent of dementia cases. Memory loss and cognitive impairment are mild in the early stages of AD, but as the disease progresses patients lose fundamental cognitive capacities, including the ability to carry out a conversation and respond to their environment. Thus, there is a strong need for simple non-invasive measures of disease progression and therapeutic response. Early diagnostic tools are especially needed, as people with mild cognitive impairment (MCI) are at higher risk for developing AD than normal elderly individuals.

SUMMARY OF THE INVENTION

The present disclosure provides systems and methods of detecting eye movements of a subject for the diagnosis of a neurological disease, such as Alzheimer's Disease (AD). In an embodiment, a method includes tracking eye movements of the subject, identifying microsaccades from the tracked eye movements, and characterizing microsaccade dynamics of the identified microsaccades to determine one or more parameters. These parameters include microsaccade direction, microsaccade velocity, microsaccade magnitude, microsaccadic peak velocity-magnitude relationship, microsaccade duration, and intersaccadic intervals. The method also includes comparing the one or more determined parameters with a corresponding healthy parameter of a healthy subject, assessing the comparison to determine statistical differences between the one or more determined parameters and the corresponding healthy parameters indicative of the presence of AD, and generating a report including the diagnosis of AD based on the assessment.

In another embodiment, the present disclosure provides a method of diagnosing Alzheimer's Disease (AD) in a subject. The method includes tracking eye movements of the subject and identifying microsaccades from the tracked eye movements. The method further includes characterizing one or more dynamics of each of the microsaccades, wherein the dynamics include a direction of the microsaccade. The method further includes comparing the one or more characterized dynamics to corresponding healthy microsaccade dynamics of a healthy subject and, from this comparison, assessing differences between the one or more determined dynamics and the corresponding healthy microsaccade dynamics to determine a presence of AD. The method further includes generating a report including one or more diagnoses related to AD of the patient, the diagnoses being based on the differences between the one or more determined dynamics and the corresponding healthy microsaccade dynamics. One of the differences indicating the presence of AD may be an average microsaccade direction that is significantly less horizontal than a corresponding average healthy microsaccade direction. The differences indicating the presence of AD may include one or more of a microsaccade velocity, microsaccade magnitude, microsaccadic peak velocity-magnitude relationship, microsaccade duration, and intersaccadic intervals that is not significantly different than the corresponding healthy microsaccade dynamics. The diagnoses may include one or both of progression of AD and response to treatment for AD, the progression of AD and the response to treatment being based on the differences as compared to previous statistical differences obtained using the method.

In another embodiment, the present disclosure provides a method of detecting a neurological disease in a subject. The method includes obtaining eye movement traces from tracked eye movements of the subject, and identifying a plurality of microsaccades in the eye movement traces. The method further includes characterizing one more dynamics of the microsaccades, the dynamics including a distribution of microsaccade directions. The method further includes assessing one or more differences between the dynamics of the microsaccades as compared to corresponding control microsaccade dynamics, and generating a report comprising one or more diagnoses related to the neurological disease based on the differences. Identifying the plurality of microsaccades may include identifying one or more square-wave jerks. The dynamics may include an index of each square-wave jerk. The distribution of microsaccade directions includes a direction for each identified microsaccade, the direction being measured as an angular deviation from horizontal. One of the differences may be an average deviation of the distribution of microsaccade directions from horizontal.

The control microsaccade dynamics may be obtained from a healthy subject, and may include a control distribution of microsaccade directions. One of the differences may be a deviation of the distribution of microsaccade directions from the control distribution. One or more of the differences may include a numerical difference representing a magnitude by which one or more of the dynamics differs from the corresponding control microsaccade dynamic. The diagnoses may include one or both of progression of Alzheimer's disease and response to treatment for Alzheimer's disease, the progression of Alzheimer's disease and the response to treatment being based on the differences as compared to previous differences for the subject. The method may further include presenting a visual stimulus to provoke measurable microsaccades in the subject's eyes, wherein obtaining the eye movement traces is accomplished by tracking the eye movements of the subject during the visual stimulus.

In another embodiment, the present disclosure provides a system that includes a host operably connected to an eye tracking device capable of recording eye movement traces from eye movements of a subject. The host may have at least one processor configured to receive the eye movement traces from the eye tracking device, identify a plurality of microsaccades from the eye movement traces, and measure one or more dynamics of each microsaccade, the dynamics including a direction measured as an angular deviation from horizontal. The processor may be further configured to compare each of the one or more dynamics to a corresponding healthy microsaccade dynamic of a healthy subject, and to assess one or more statistical differences between the one or more determined dynamics and the corresponding healthy microsaccade dynamics, the statistical differences being indicative of the presence of a neurological disease. The processor may be configured to generate a report including one or more diagnoses relating to the neurological disease based on the assessment. The processor may be further configured to assess the one or more statistical differences by determining whether the statistical difference is within a normal limit, and the diagnoses may include an indication that the neurological disease may be present if the statistical difference is outside of the normal limit. The processor may be further configured to assess the statistical differences by comparing the statistical differences to corresponding previous statistical differences to characterize one or both of progression of the neurological disease and response to treatment for the neurological disease. The one or more diagnoses may include one or both of the progression and the response. The neurological disease may be Alzheimer's disease.

A system in accordance with the present invention includes an eye tracking device and a host operably connected to the eye tracking device. The eye tracking device is capable of detecting eye movement traces and the host is configured to receive the eye movement traces from the eye tracking device. The host is further configured to identify microsaccades from the detected eye movement traces, and characterize microsaccade dynamics of the identified microsaccades to determine one or more parameters including microsaccade direction, microsaccade velocity, microsaccade magnitude, microsaccadic peak velocity-magnitude relationship, microsaccade duration, and intersaccadic intervals. The host is also configured to compare the one or more determined parameters with a corresponding healthy parameter of a healthy subject, assess the comparison to determine statistical differences between the one or more determined parameters and the corresponding healthy parameters indicative of the presence of AD, and generate a report including the diagnosis of AD based on the assessment.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
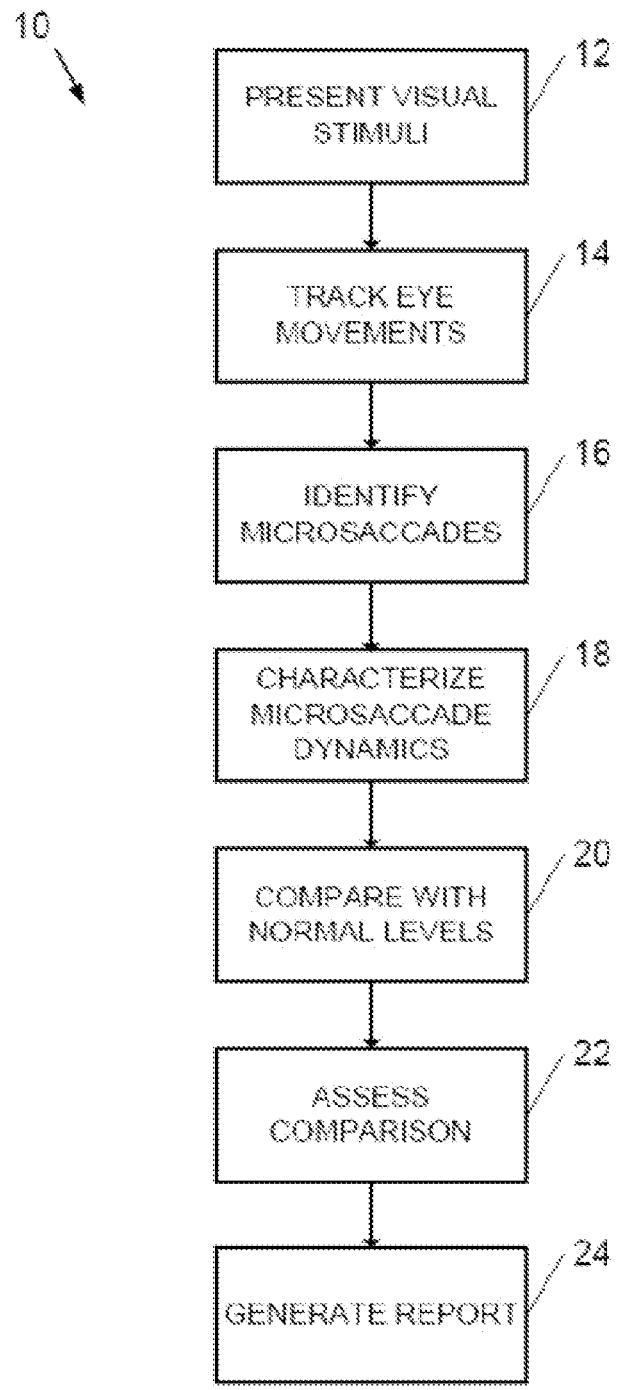
FIG. 1 is a flow chart setting forth the steps of a method for non-invasively detecting a neurological disease, in accordance with the present invention.

The eyes do not stay perfectly still during visual fixation. Rather, when a human fixates their gaze, the eyes are only actually fixated 80% of the time while saccades (quick, simultaneous movements of both eyes in the same direction) and microsaccades (rapid involuntary saccades that occur several times each second during fixation, usually less than 1 degree in magnitude) occur the other 20% of the time. Fixational eye movements as a whole (that is, both saccades and microsaccades) enhance fine spatial acuity. With further reference to microsaccades, these rapid, small-magnitude involuntary eye movements counteract visual fading and generate strong neural transients in the early visual system. Microsaccades may also drive perceptual flips in binocular rivalry. Microsaccade rates and directions are moreover modulated by attention, and thus generate rich spatio-temporal dynamics. In certain neurological disorders, attempted fixation results in abnormal fixational eye movements with distinctive characteristics. Thus, determining how normal fixation differs from pathological fixation has the potential to aid early and differential non-invasive diagnosis of neurological disease as well as the quantification of its progression and response to treatment.

The most common type of saccadic intrusion is referred to as a square wave jerk (SWJ). SWJs are characterized by one small horizontal saccadic movement that moves the eye away from the fixation target, followed by a corrective saccade towards the target shortly thereafter. SWJs are prevalent in some neurological diseases such as progressive supranuclear palsy (PSP). However, they are also common in normal subjects. For example, in U.S. Pat. No. 8,348,428, the entire content of which is incorporated herein by reference, a process is described that automatically identifies SWJs in the eye movements of a subject during visual fixation of a small target. The results show that SWJs are common in both PSP patients and healthy subjects. However, several SWJ parameters (such as SWJ rates, magnitudes, percentage of small saccades that are part of SWJs, average inter-saccadic intervals for the SWJs, saccadic rates, saccadic peak velocities within SWJs, standard deviation of the direction difference between pairs of saccades in the SWJs, standard deviation of the difference between the horizontal and the direction of the saccades in the SWJs) are found to be different in the PSP group. As a result, the objective characterization of SWJs may provide a powerful tool in the differential diagnosis of various oculomotor diseases.

While past research has examined saccadic eye movements and SWJs in relation to oculomotor disease, little research has been done to examine the characteristics of microsaccades in various oculomotor diseases, such as Alzheimer's Disease (AD) and mild cognitive impairment (MCI, which may include amnesic mild cognitive impairment (aMCI)). The present invention provides a method and system for monitoring eye movements and, in particular, microsaccades of a subject to detect AD and/or MCI. Generally, the method includes determining abnormal fixational eye movements, such as microsaccades, as an indication of neurological disease (for example, AD or MCI) and/or quantifying the abnormality to determine disease progression and/or response to treatment. More specifically, the system and method include measuring microsaccades of a subject and analyzing microsaccade parameters and dynamics, such as microsaccade direction, microsaccade velocity, microsaccade magnitude, microsaccadic peak velocity-magnitude relationship, microsaccade duration, and/or intersaccadic intervals, for the differential diagnosis of AD and/or MCI as well as disease progression and/or response to treatment.

Figure 4:
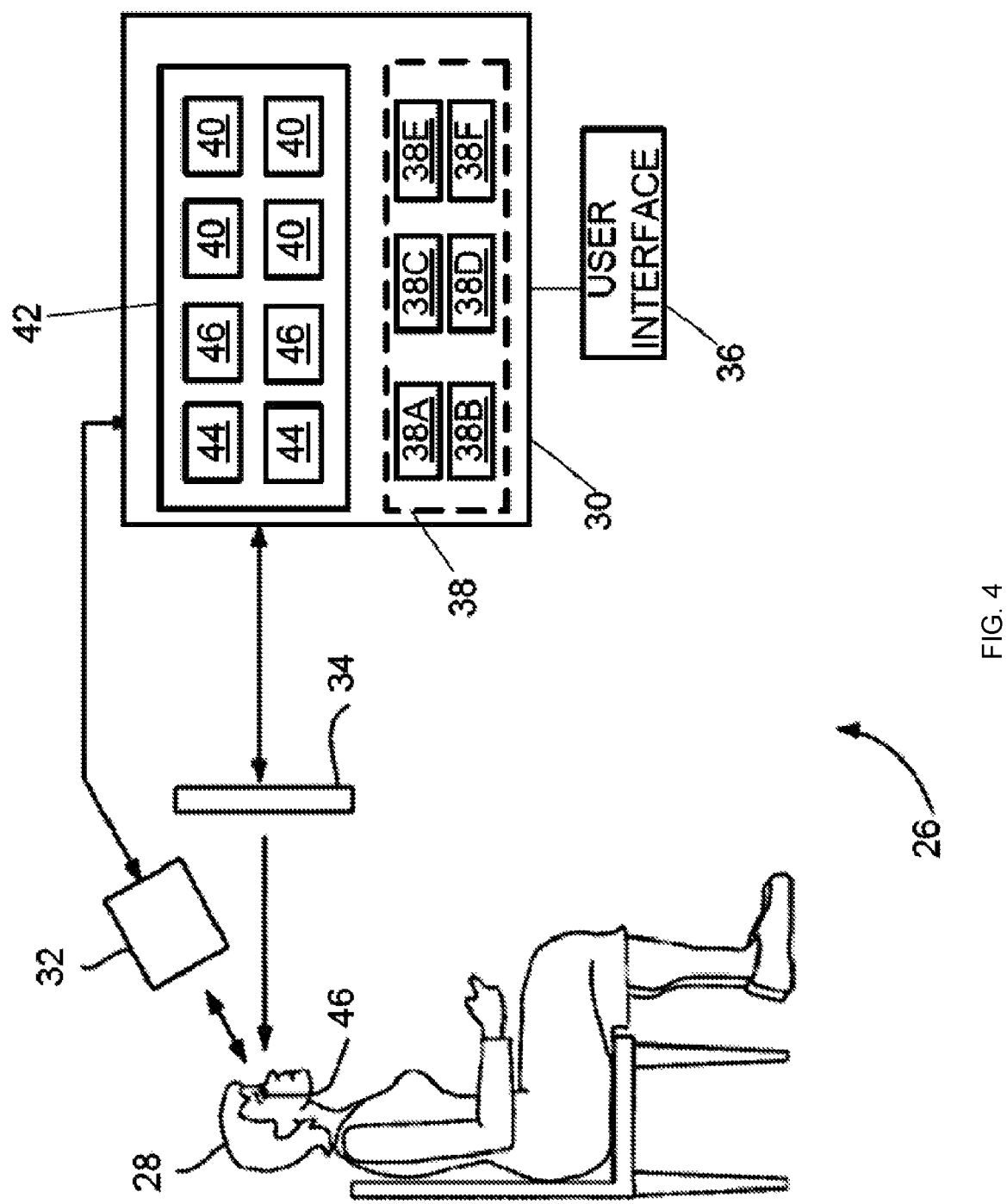
FIG. 4 is a schematic view of a system according to the present invention.

FIG. 1 illustrates a method 10, in accordance with the present invention, for non-invasively monitoring eye movements for the differential diagnosis of AD and/or MCI. The method 10 may be carried out using a system 26, as shown in FIG. 4 and described below. As shown in FIG. 1, the method 10 can include presenting visual stimuli to a patient (process block 12). For example, visual stimuli can be presented on a display screen about 40 centimeters away from a subject's eyes. Presentation of visual stimuli may begin with a five-point calibration sequence followed by the presentation of a small fixation cross (for example, 1 degree) at the center of the screen. The fixation cross can remain displayed for about 20 seconds, and the subject can be instructed to look at the fixation cross as accurately as possible. During this time, the subject's eye movements can be tracked (process block 14), such as with an eye tracking device as described below. Microsaccades can be identified from the tracked eye movements (process block 16), for example through an objective detection algorithm (e.g., Engbert and Kliegl, 2003; Martinez-Conde, Macknik, Hubel, 2000). Based on the identified microsaccades, microsaccade dynamics can be characterized and/or measured (process block 18). Such microsaccade dynamics can include, but are not limited to, microsaccade direction, microsaccade velocity, microsaccade magnitude, microsaccadic peak velocity-magnitude relationship, microsaccade duration, and/or intersaccadic intervals.

In some implementations, process blocks 16 and 18 can also or alternatively include identifying and characterizing (respectively) SWJs. Generally, as described above, a SWJ may be defined as the combination of one small saccade that moves the eye away from the fixation target, followed after a short period by a second corrective saccade directed back towards the target. More specifically, a SWJ is known in the art to be a pair of saccades with three defining characteristics: (1) the two saccades have opposite or nearly opposite directions; (2) both saccades have equal or nearly equal magnitudes; and (3) the two saccades are separated by a short interval. An example process for identifying and characterizing SWJs is described in U.S. Pat. No. 8,348,428, the entire content of which is incorporated herein by reference. This process measures how similar a given saccade pair (that is, a pair of consecutive saccades) is to an "ideal SWJ", based on the three defining characteristics of SWJs described above, and gives the saccade pair an score, or "index," for its measurements relative to the ideal SWJ. If a saccade pair's SWJ index is larger than a given threshold, it may be characterized as a potential SWJ.

Referring back to FIG. 1, one or more of the above-described microsaccade dynamics (and/or SWJ dynamics) can be compared with dynamics of healthy subjects, considered "normal levels," (process block 20) and such comparisons are then assessed (process block 22). Assessment of the comparisons can include, but is not limited to, assessing a statistical difference (for example, within or not within normal limits, as determined by a significant or non-significant difference), quantifying the magnitude of a difference (that is, a numerical difference), etc. Comparison (process block 20) and assessment (process block 22) are further described in general and with respect to a particular example study below. Following the assessment, a report may be generated (for example, recorded, stored, and/or displayed) providing a diagnosis and/or other information based on the assessment (process block 24). For example, the report may designate the presence or absence of oculomotor disease (that is, AD or MCI), a quantification of abnormality signifying disease susceptibility, progression, severity, and/or response to treatment or therapy, etc.

For example, microsaccade direction is significantly different in subjects with AD or aMCI versus healthy subjects. In particular, the average microsaccade direction may be significantly deviated from horizontal, or from that of healthy subjects, by 20 degrees or more, although a smaller deviation may still be significant when considered with other factors. An example study was performed to demonstrate this relationship. The example study included three subject populations: patients with aMCI, patients with AD, and age-matched normal subjects. The AD patients suffered from AD of mild to moderate severity, without ophthalmological or other neuropsychiatric disorders. All subjects had normal or corrected-to-normal visual acuity without group difference by age or gender, and each subject produced a minimum of 50 microsaccades during the experiment. Most of the patients were not taking anti-dementia medication, though a few cases were enrolled in a clinical trial (blind and placebo controlled) for AD medication. The participants consisted of 18 subjects (4 men) with AD (60 to 83 years old; mean 72±9 years), 15 subjects (5 men) with aMCI (59 to 91 years old; mean 76±11 years), and 21 age- and education-matched healthy controls (9 men; 60 to 93 years old; mean 73±9 years). All clinical characteristics of subjects, including the estimated duration of disease and the degree of autonomy measured by the Activities of Daily Living (ADL) scale are summarized in Table 1.

TABLE 1

SUBJECT DEMOGRAPHICS, MICROSACCADE CHARACTERISTICS, AND STATISTICAL COMPARISONS

| | Controls | MCI | AD | p-value (ANOVA) |
|---|---|---|---|---|
| Subject demographics (mean ± SD) | | | | |
| N | 21 | 15 | 18 | NA |
| Age (years) | 73 ± 9 | 76 ± 11 | 72 ± 9 | 0.4 |
| Gender (m/f) | 9/12 | 5/10 | 4/14 | NA |
| Education (years) | 11 ± 3 | 12 ± 4 | 10 ± 4 | 0.2 |
| MMSE | 29 ± 1 | 26 ± 2 | 16 ± 4 | $2 \times 10^{-16}$ |
| ADL (Max.56) | 15 ± 4 | 17 ± 4 | 29 ± 9 | $5 \times 10^{-9}$ |
| Estimated duration of disease (years) | NA | 3.3 ± 2.7 | 4.5 ± 3.0 | NA |
| Microsaccade characteristics (mean ± SD) | | | | |
| Rate (N/s) | 1.78 ± 0.13 | 1.69 ± 0.14 | 1.45 ± 0.14 | 0.2 |
| Magnitude (deg) | 0.98 ± 0.39 | 1.04 ± 0.46 | 1.12 ± 0.57 | 0.6 |
| Peak velocity (deg/s) | 50.9 ± 16.3 | 57.3 ± 24.6 | 61.2 ± 28.6 | 0.4 |
| Duration (ms) | 35.7 ± 7.2 | 32.9 ± 5.9 | 32.2 ± 8 | 0.3 |
| Intersaccadic interval (ms) | 391 ± 114 | 357 ± 72 | 405 ± 165 | 0.5 |
| Direction (deviation from horizontal, deg) | 27.6 ± 9.2 | 36.2 ± 11.7 | 37.1 ± 10.7 | 0.011 |
| SWJ rate | 0.74 ± 0.07 | 0.74 ± 0.09 | 0.68 ± 0.1 | 0.8 |
| Percent of saccades in SWJs (%) | 43 ± 4 | 42 ± 3 | 44 ± 3 | 0.9 |

TABLE 1-continued

SUBJECT DEMOGRAPHICS, MICROSACCADE
CHARACTERISTICS, AND STATISTICAL
COMPARISONS

|  | Controls | MCI | AD | p-value (ANOVA) |
|---|---|---|---|---|
| SWJ magnitude (deg) | 1.06 ± 0.09 | 1.04 ± 0.13 | 1.16 ± 0.16 | 0.8 |
| SWJ direction (deviation from horizontal, deg) | 21.4 ± 2.7 | 32.8 ± 3.8 | 31.3 ± 3.5 | 0.03 |

Visual stimuli were presented (process block 12) on a PC screen 40 cm away from the subjects. Experiments started with a 5-point calibration sequence, followed by the presentation of a small fixation cross (1 deg) on the center of the screen. The fixation cross remained onscreen for 20 seconds, and subjects were required to look at it as accurately as possible; this was repeated four times. Eye movements were recorded (process block 14) binocularly with the Eye See Cam at a sampling rate of 220 Hz (resolution 0.01° RMS).

Microsaccades were identified (process block 16) automatically with an objective detection algorithm (see (Engbert and Kliegl, 2003), for details). In subjects in whom eye position was recorded binocularly, the amount of potential noise in the recorded movements was reduced (Engbert, 2006) by considering only binocular microsaccades microsaccades with a minimum overlap of one data sample in both eyes). Some microsaccades are followed by a fast, small, oppositely directed, saccadic eye movement called dynamic overshoot, which is often more prominent for the eye that moves in the abducting direction. Dynamic overshoots that occurred less than 20 ms after a preceding microsaccade were interpreted as part of the preceding microsaccade. That is, the previous microsaccade was modified to include the dynamic overshoot, which was not itself counted as a discrete microsaccade.

Microsaccade identification was improved in the study by removing, prior to microsaccade identification, any data epochs where partial pupil occlusion may have led to increased levels of noise. Such epochs were automatically identified by identifying high-velocity spikes in the eye movement data (specifically, over 1,000 deg/s, although epochs of as little as 25 deg/s could be removed). When two epochs were separated by less than 25 samples, they could be merged into a single epoch, which included the interval separating the two original epochs.

Characterization of eye movement dynamics was improved as described above by including SWJs in the analysis. SWJs were identified by first identifying all individual saccades up to 5 degrees (Otero-Millan, Serra, et al., 2011). The 5-degree upper magnitude threshold was chosen to include the range of SWJ magnitudes reported previously in healthy subjects (0.1-4.1 deg; (Abadi and Gowen, 2004)), and to allow for potentially larger SWJs magnitudes in patients (Otero-Millan, Serra, et al., 2011). Subsequently saccade pairs were indexed based on the three defining characteristics of SWJs described above: a) the direction dissimilarity of first and second saccade, b) the magnitude similarity of first and second saccade, and c) the temporal proximity of first and second saccade, in a single, continuous variable for each saccade pair. If a saccade pair's SWJ index was larger than a given threshold (Otero-Millan, Serra, et al., 2011) the pair was classified as a potential SWJ.

Figure 2C:
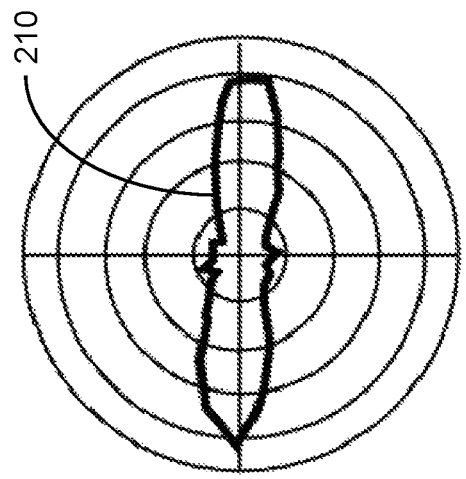
FIGS. 2A-C are graphical representations of microsaccade directions in an eye movement trace for Alzheimer's disease, mild cognitive impairment, and control subject populations, respectively.
Figure 2B:
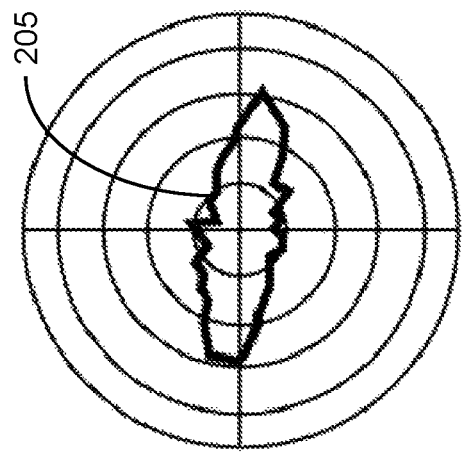
Figure 2A:
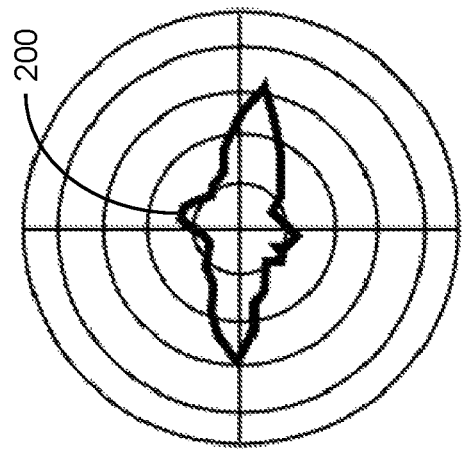
Figure 3B:
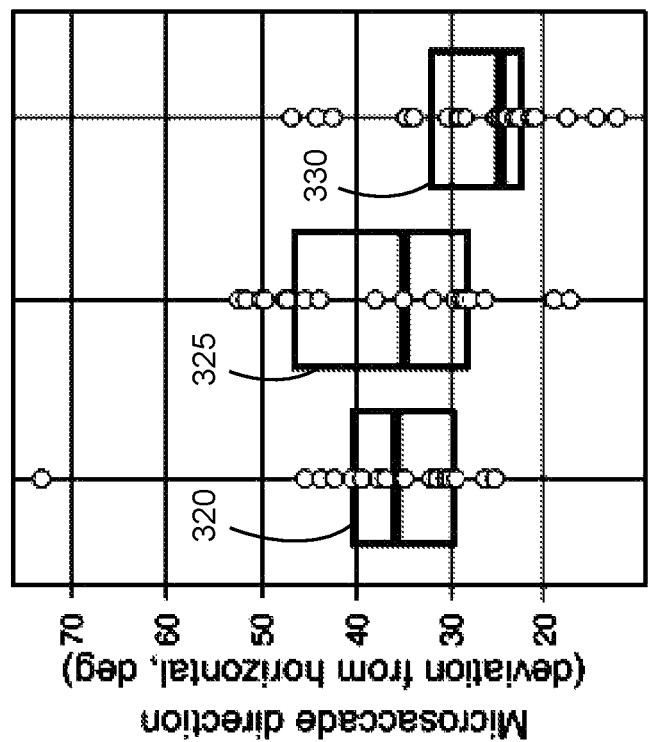
FIGS. 3A-B are charts relating microsaccade direction among the subject populations represented in the graphical representations of FIGS. 2A-C.
Figure 3A:
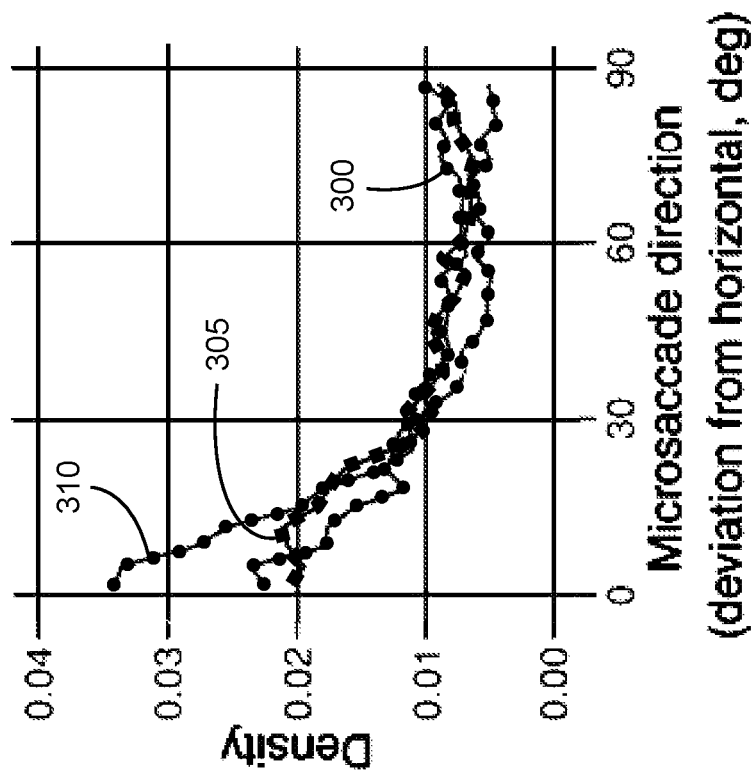

The identified microsaccades were then characterized (process block 18). FIGS. 2A-C are polar histograms showing microsaccadic direction (shown in bold lines 200, 205, 210) in the AD population (FIG. 2A), the aMCI population (FIG. 2B), and the healthy population (FIG. 2C). FIG. 3A is a line graph of the distribution of microsaccades at increasing deviation from horizontal for the three populations, where the AD population is represented by line 300, the aMCI population by line 305, and the healthy population by line 310. FIG. 3B is a deviation graph also showing the average microsaccade direction as a deviation from horizontal, with the AD population represented by group 320, the aMCI population by group 325, and the healthy population by group 330. The results show that, despite predominantly horizontal microsaccade directions across all subject populations, oblique microsaccades (that is, less horizontal microsaccades) are more prevalent in AD and aMCI subjects than in age-matched healthy subjects. Furthermore, the differences in microsaccade directions between AD or aMCI subjects and healthy subjects extended to those microsaccades forming SWJs. Previous research has suggested a continuum from microsaccades to SWJs, in which larger microsaccades away from the center of gaze trigger a corrective return microsaccade (Otero-Millan, Macknik, et al., 2011; Otero-Millan, Serra, et al., 2011). The present results are consistent with this hypothesis, and suggest that microsaccades and square-wave jerks share a common generator, both in the healthy brain and in neurological disease.

In contrast, microsaccade magnitudes and velocities, and the peak velocity-magnitude relationship, are comparable in the three subject groups (that is, AD, aMCI, healthy). Microsaccadic durations, intersaccadic intervals and other microsaccade dynamics are also equivalent (and have comparable variability) in the three groups, as are the rate, magnitude, and percent of fixational saccades that are part of SWJs. This finding is consistent with the lack of brainstem oculomotor function impairment in MCI or AD patients with mild to moderate severity of disease (Garbutt et al., 2008; Yang et al., In Press; Yang et al., 2011; but see Simic et al., 2009).

In some implementations, all the above dynamics (that is, significant statistical differences as well as non-significant statistical differences) may be collectively assessed to determine presence or absence of oculomotor disease (that is, AD or MCI), disease susceptibility, progression, severity, and/or response to treatment, etc. Accordingly, an assessment of significantly less horizontal microsaccade direction, but normal (that is, not significantly different) microsaccade magnitudes, velocities, peak velocity-magnitude relationship, microsaccadic durations, and intersaccadic intervals results in a diagnosis of AD or MCI. This assessment can further quantify the obliqueness of the microsaccades in comparison to healthy levels to determine a progression of AD or MCI, response to treatment (for example, if the subject's previously tracked microsaccade dynamics are available for comparison), etc. The generated report can therefore detail the diagnosis as well as the assessment of progression and/or response to treatment.

In addition, the above method may include receiving additional input regarding the subject, including demographics such as age, gender, education, results of a mini mental state examination (MMSE) and/or activities of daily living (ADL) to assist in the above-described assessment. For example, Table 1 illustrates a comparison of demographics and microsaccade dynamics of healthy subjects ("controls"), MCI subjects, and AD subjects according to a study carrying out the methods of the present invention. Any or all of the demographics, characteristics, and/or statistical comparisons detailed in the table below may be presented in the generated report.

FIG. 4 illustrates a system 26, according to the present invention, for detecting and analyzing eye movements of a subject 28 to diagnose neurological disease. The system 26 may be used in accordance with the methods 10 described above. As shown in FIG. 4, the system 26 can include a host 30 operably connected to an eye tracking device 32, a display 34, and a user interface 36. The host 30 can include one or more processors 38 operating under control of one or more computer programs 40 loaded from a non-transitory computer readable medium (memory) 42. As used herein, reference to a step performed by a computer program 40 is also a reference to the processor 38 that performed that step, for example in accordance with process blocks of above-described methods 10 of the present invention. Example tracking devices 32 for use with the present invention can include the EyeLink II by SR Research or other equivalent eye tracking systems such as the IVIEW X™ HI-SPEED 1250 tracking system by SensoMotoric Instruments.

The system 26 can operate by presenting visual stimuli to the subject 28 through the display 34. For example, one of the processors 38, such as a display processor 38A, can retrieve one or more stored image or video files 44 from memory 42 and present the images/videos to the subject 28 via the display 34. As the images/videos are presented to the subject 28, the eye tracking device 32 can detect the position and movement of the subject's eyes 46, for example, in accordance with process block 14 described above. Identification of microsaccades, for example with respect to process block 16 described above, can be executed by one or more processors 38. An example process where eye movements are objectively and non-invasively monitored is described in U.S. Pat. No. 7,857,452, the entire contents of which is incorporated herein by reference. Generally, this process includes tracking a subject's eye position, for example, using a tracking processor 38B, and detecting microsaccades from eye position traces, for example, using a microsaccade processor 38C. Example algorithms (that is, part of computer programs 40) for detecting microsaccades objectively from eye position traces (such as from video, eye coil, optical, or other suitable tracking methods) include the Martinez-Conde and Macknik algorithm (Martinez-Conde S., Macknik S. L., Hubel D. H. (2000) Nature Neuroscience, incorporated herein by reference) and the Engbert algorithm (Engbert R., Kliegl R. (2003) Vision Res 4:1035-1045, incorporated herein by reference).

In addition, characterization and analysis of microsaccade dynamics, for example with respect to process blocks 18-22 described above, can be executed by one or more processors 38, such as the microsaccade processor 38C, a statistics processor 38D, and/or a comparator 38E. In some implementations, additional processors 38 may be included to execute identification and analysis of SWJs. Furthermore report generation, for example with respect to process block 24 described above, can be executed by one or more processors 38, such as a reporting processor 38F, wherein the report may be stored in a file 44 in memory 42, displayed on the display 34 or a separate display, or output in another suitable manner to a user, for example as instructed by the user via the user interface 36.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for analyzing eye movements of a subject, the system comprising:
    an eye tracking device configured to track eye movements of the subject;
    a display; and
    a processor in communication with the eye tracking device and the display, the processor configured to:
        cause the display to present a visual stimulus to the subject;
        cause the eye tracking device to track eye movements of the subject;
        identify fixational eye movements from the tracked eye movements, the fixational eye movements including one of microsaccades and square wave jerks, wherein a microsaccade is defined as having a magnitude of less than 1 degree;
        analyze the fixational eye movements of the subject; and
        determine at least one of a presence, an absence, a severity, a progression, and a response to treatment of a neurological disease based on the analyzed fixational eye movements, the neurological disease being one of Alzheimer's Disease and Mild Cognitive Impairment.

2. The system of claim 1, wherein the fixational eye movements include microsaccades and the processor is configured to:
    determine a microsaccade direction based on the microsaccades, the microsaccade direction being an angular deviation from horizontal; and
    determine at least one of the presence, the absence, the severity, the progression, and the response to treatment based on the microsaccade direction.

3. The system of claim 2, wherein the processor is configured to determine the microsaccade direction from each of the identified microsaccades and calculate an average microsaccade direction.

4. The system of claim 3, wherein the processor is configured to determine at least one of the presence, the absence, the severity, the progression, and the response to treatment by comparing the average microsaccade direction to a control microsaccade direction.

5. The system of claim 4, wherein the control microsaccade direction is one of an average microsaccade direction of a healthy subject and an average microsaccade direction previously tracked from the subject.

6. The system of claim 3, wherein the processor is configured to determine the presence of the neurological disease based on the average microsaccade direction being significantly less horizontal than an average microsaccade direction of a healthy subject.

7. The system of claim 1, wherein the processor is further configured to determine an additional microsaccade dynamic including at least one of a microsaccade magnitude, a microsaccade velocity, a microsaccade peak velocity-magnitude relationship, a microsaccade duration, and an intersaccadic interval based on the microsaccades; and
    determine at least one of the presence, the absence, the severity, the progression, and the response to treatment based on the microsaccade direction and the additional microsaccade dynamic.

8. The system of claim 1, wherein the fixational eye movements include square wave jerks and the processor is configured to:

determine a square wave jerk direction based on the square wave jerks, the square wave jerk direction being an angular deviation from horizontal; and determine at least one of the presence, the absence, the severity, the progression, and the response to treatment based on the square wave jerk direction.

9. The system of claim 8, wherein the processor is configured to determine the square wave jerk direction from each of the identified square wave jerks and calculate an average square wave jerk direction.

10. The system of claim 9, wherein the processor is configured to determine at least one of the presence, the absence, the severity, the progression, and the response to treatment by comparing the average square wave jerk direction to a control square wave jerk direction.

11. The system of claim 10, wherein the control square wave jerk direction is one of an average square wave jerk direction of a healthy subject and an average square wave jerk direction previously tracked from the subject.

12. The system of claim 9, wherein the processor is configured to determine the presence of the neurological disease based on the average square wave jerk direction being significantly less horizontal than an average square wave jerk direction of a healthy subject.

13. The system of claim 8, wherein the processor is further configured to determine an additional eye movement dynamic including at least one of a microsaccade magnitude, a microsaccade velocity, a microsaccade peak velocity-magnitude relationship, a microsaccade duration, and an intersaccadic interval based on the fixational eye movements; and determine at least one of the presence, the absence, the severity, the progression, and the response to treatment based on the square wave jerk direction and the additional eye movement dynamic.

14. The system of claim 1, wherein the processor is configured to track the eye movements of the subject as the subject fixates on the visual stimulus.

15. The system of claim 1, wherein the processor is further configured to generate a report including information indicative of the determination of at least one of the presence, the absence, the severity, the progression, and the response to treatment and display the report via the display.

* * * * *

UNITED STATES PATENT AND TRADEMARK OFFICE
CERTIFICATE OF CORRECTION

PATENT NO. : 11,903,720 B2
APPLICATION NO. : 16/741549
DATED : February 20, 2024
INVENTOR(S) : Stephen L. Macknik et al.

It is certified that error appears in the above-identified patent and that said Letters Patent is hereby corrected as shown below:

In the Specification

Column 7, Lines 28-29, "microsaccades microsaccades" should be --microsaccades (i.e., microsaccades--.

Signed and Sealed this
Twenty-third Day of April, 2024

Katherine Kelly Vidal
*Director of the United States Patent and Trademark Office*